United States Patent [19]

Hirose et al.

[11] Patent Number: 4,514,395
[45] Date of Patent: Apr. 30, 1985

[54] PHENOTHIAZINE DERIVATIVES AND ANTI-PSYCHOTIC DRUGS CONTAINING THE SAME

[75] Inventors: Noriyasu Hirose, Tokyo; Shizuo Kuriyama, Saitama; Kiyomi Yamatsu, Kanagawa; Akifumi Kitahara; Takeshi Uzuo, both of Saitama, all of Japan

[73] Assignee: Eisai Ci., Ltd., Tokyo, Japan

[21] Appl. No.: 123,008

[22] Filed: Feb. 20, 1980

[30] Foreign Application Priority Data

Feb. 22, 1979 [JP] Japan .................................. 54-19052

[51] Int. Cl.³ ..................... A61K 31/54; C07D 417/06
[52] U.S. Cl. ........................................ 514/224; 544/46
[58] Field of Search ........................... 544/46; 424/247
[56] References Cited

U.S. PATENT DOCUMENTS

| | | | |
|---|---|---|---|
| 3,075,976 | 1/1963 | Jacob et al. | 544/46 |
| 3,193,549 | 7/1965 | Zenitz | 544/46 |
| 3,320,243 | 5/1967 | Habicht et al. | 544/46 |
| 3,961,055 | 6/1976 | Baget | 544/46 X |
| 3,966,930 | 6/1976 | Buus et al. | 544/46 X |
| 4,018,922 | 4/1977 | Derible et al. | 544/46 X |
| 4,139,632 | 2/1979 | Hirose et al. | 424/247 |

FOREIGN PATENT DOCUMENTS

| | | | |
|---|---|---|---|
| 834370 | 5/1960 | United Kingdom | 544/46 |
| 1013909 | 12/1965 | United Kingdom | 544/46 |

*Primary Examiner*—Joseph Paul Brust
*Attorney, Agent, or Firm*—Wyatt, Gerber, Shoup, Scobey and Badie

[57] ABSTRACT

New phenothiazine derivatives having the general formula:

wherein R represents a straight or branched alkyl group or alkenyl group having 5–15 carbon atoms, their acid addition salts and anti-psychotic drugs containing such new compounds.

11 Claims, No Drawings

PHENOTHIAZINE DERIVATIVES AND ANTI-PSYCHOTIC DRUGS CONTAINING THE SAME

The present invention relates to new phenothiazine derivatives having the general formula:

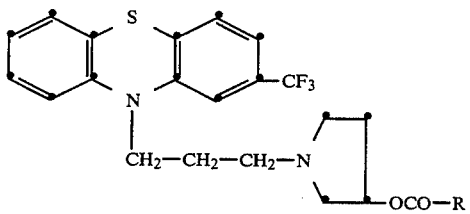

wherein R represents a straight or branched alkyl group or alkenyl group having 5-15 carbon atoms, their acid pharmaceutically acceptable addition salts useful for medical treatment, and anti-psychotic drugs, containing such new compounds.

In the above formula (I), there may be mentioned, as an alkyl, alkenyl or aralkyl group, for example, benzyl, hexyl, heptyl, octyl, nonyl, decyl, undecyl, dodecyl, tridecyl, tetradecyl, pentadecyl, 1-methyl-butyl, 1-ethyl-benzyl, 1-pentenyl, 1-octenyl, 9-decenyl and the like.

The expression of "acid addition salts" means, for example, pharmaceutically acceptable salts of inorganic acid such as hydrochloride, hydrobromide, sulphate and the like; and salts of organic acid such as oxalate, citrate, tartarate, methanesulfonate and the like.

The derivatives of the present invention represented by the general formula (I) may be produced by several synthetic routes, by taking the chemical structure of the derivatives (I) into consideration. Typical process for the production of the derivatives (I) comprises the reaction of 2-trifluoromethyl-10-[3-(3-hydroxypyrrolidino)-propyl]-phenothiazine of the general formula (II):

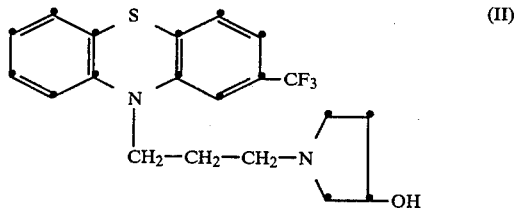

with carboxylic acids of the general formula (III):

R—COOH   (III)

wherein R has the same meanings as defined above or the reactive derivatives thereof.

In case of using carboxylic acid per se at that time, it is preferable to use the condensing agents such as dicyclohexylcarbodiimide, polyphosphoric acid, phosphorous oxychloride, tosyl chloride and the like. As reactive derivatives of carboxylic acid, there may be used the carboxylic acid in the converted form of carboxylic acid such, for example, as acid chloride, acid anhydride, mixed acid anhydride and the like. The reaction may be carried out with or without using a solvent. Such solvent can be properly selected from the inactive organic solvents such as dichloromethane, dichloroethane, trichloroethane, chloroform, benzene, toluene, xylene and the like.

The new phenothiazine derivatives (I) of the present invention have an interesting pharmacological activity, that is to say, psychotropic activities having the durable action.

The compound having the general formula (II), which is a starting material to be used for the production of the phenothiazine derivatives (I), falls within the scope of the sorts of phenothiazine derivatives described in our U.S. Pat. No. 4,139,632. This compound has been very expected as a low-toxic and less side effect psychotropic drug useful for the improvement of schizophrenia and acute or chronic psychosis; the improvement of aniety and tension accompanied by neurosis, mania, depression and the like; the treatment and prevention of nausea (vomiturition) and vomiting. As the result of a further study for the purpose of lowering toxicity and durability of action, we have accomplished the expected objects as shown in the following pharmacological tests.

PHARMACOLOGICAL TEST

The test compound

The following compounds were selected as test compounds.

2-Trifluoromethyl-10-[3-(3-caproyloxypyrrolidino)-propyl]-phenothiazine (hereinafter referred to the compound A of the present invention)

2-Trifluoromethyl-10-[3-(3-enanthyloxypyrrolidino)-propyl]-phenothiazine (hereinafter referred to the compound B of the present invention)

2-Trifluoromethyl-10-[3-(3-hydroxypyrrolidino)-propyl]-phenothiazine (hereinafter referred to the known compound (a))

The test compounds were prepared in an injectable form with sesame oil as a solvent.

Methods and Results (1) Cataleptogenic activity

Male Spargue-Dawley rats having the body weights of about 300 g were treated subcutaneously with 20 mg/Kg of the test compounds. The symptom of catalepsy was observed for 21 days after the administration according to the method of Delini-Stule et al. (Int. J. Neuro-pharmacol. 7, 371, 1968).

Table 1 shows the onset and the duration of catalepsy by the test compounds.

TABLE 1

| Test compound | Number of animals used | Onset (hours) | Duration (days) |
| --- | --- | --- | --- |
| Compound A of the present invention | 5 | 5 | 8 |
| Compound B of the present invention | 5 | 5 | 22 |
| Known compound (a) | 5 | 0.5 | 1 |

It is apparent that the onsets of the cataleptogenic action of the compounds A and B of the present invention were later than that of the known compound (a), but their durations of action were very longer than that of the known compound (a).

(2) Apomorphine antagonism

Male mongrel dogs having the body weights of 10-13 Kg were intramuscularly given the test compounds with a dose of 10 mg/Kg. The antagonistic activity of the test compounds was tested against vomiting induced by apomorphine 0.1 mg/Kg subcutaneously (s.c.) with appropriate intervals during a period of 28 days. Five animals were used per each of the test compounds.

The compound A of the present invention showed significant antagonism against apomorphine-induced vomiting at 3 and 7 days after administration, and its effect lasted for 7–14 days. Further, the compound B of the present invention had more long-lasting anti-apomorphine effect, which was still observed at 14–21 days after administration.

(3) Toxicity

Male Spargue-Dawley rats having the body weights of 300–400 g were treated with subcutaneous doses of the test compounds. During 14 days following administration, the changes of the body weight, toxic symptoms and lethal rate were observed. The results were showen in Table 2.

TABLE 2

| Test Compound | Number of animals used | Lethal dose (mg/Kg) | Just administration | After 1 day | After 2 days | After 14 days |
|---|---|---|---|---|---|---|
| Compound A of the present invention | 5 | >1,000 | 332 ± 8.2 | 303 ± 7.5 | 247 ± 11.5 | 272 ± 31.4 |
| Compound B of the present invention | 5 | >1,000 | 354 ± 6.9 | 332 ± 5.7 | 290 ± 14.4 | 328 ± 18.1 |
| Known Compound[a] | 5 | >300 | 350 ± 7.6 | 323 ± 8.7 | 247 ± 4.6 | 324 ± 7.2 |

In cases of the compounds A and B of the present invention, no death was observed with a high dose of 100 mg/Kg, but the body weight gradually decreased during 6 days following administration, and therefore showed a recovery. Moreover, the gross behavioral changes such as hypomotility, sedation, catalepsy, potasis, and hypothermia were observed for about 14 days.

On the other hand, no death was observed following administration of 300 mg/Kg s.c. of the known compound (a). However, there were observed the toxic symptoms such as general debility, piloerection, lacrimation, diarrhea, hypothermia, ataxia, sedation, catalepsy and the like. These symptoms of the known compound (a) were more profound, as compared with those of the compounds A and B of the present invention.

The compound (I) of the present invention may be administered in the form of several drugs containing an anti-phychotically effective amount of a compound of this invention together with a pharmaceutically acceptable excipient, particularly, an injection drug (non-aqueous injection) dissolved in non-aqueous solvent. These non-aqueous solvents for using in non-aqueous injection include those which may usually used in the production of non-aqueous injection, for example, vegetable oils such as olive oil, sesame oil, soybean oil, camellia oil, rapeoil, corn oil, peanut oil, cotton seed oil and the like, and aqueous organic solvents such as ethanol, propylene glycol, polyethylene glycols and the like. If desired, there may be added local anesthesia agents as indolent drugs such as procaine hydrochloride, xylocain hydrochloride and the like, or antiseptics such as benzyl alcohol, phenol and the like.

Following Examples will serve to illustrate the present invention, but should be construed that the invention is not restricted by these Examples.

EXAMPLE 1

Production of 2-trifluoromethyl-10-[3-(3-decanoyloxypyrrolidino)-propyl]-phenothiazine (i) 10.0 Grams of 2-trifluoromethyl-10-[3-(3-hydroxypyrrolidino)-propyl]-phenothiazine.hydrochloride were dissolved in 100 ml of dry chloroform. To the solution were added drop by drop 4.5 g of decanoylchloride at a room temperature with stirring. After finishing the dropping procedure, the mixture was heated under reflux for six hours. Then, the solvent was removed by distillation under a reduced pressure. To the residue were added 100 ml of water. 10% aqueous sodium hydroxide solution was added under cooling to the solution, so as to make it basic. The isolated oily material was extracted with benzene. The extracted layer was washed with water, and dried over sodium sulphate. The solvent was then distilled off under a reduced pressure. The residue was dissolved in 50 ml of acetone. To the solution were added 3 g of oxalic acid. The whole was heated for 30 minutes. After cooling, the deposited crystalline mass was recovered by filtration and recrystallized from acetone. The oxalate of the object was thus obtained.

Melting point: 113°–115° C.

Yield: 12.7 g.

Measurement value of infrared absorption spectrum: $v_{max}^{Nujol}$ cm$^{-1}$ 1736 (Ester).

(ii) 32 Grams of 2-trifluoromethyl-10-[3-(3-decanoloxypyrrolidino)-propyl]-phenothiazin.oxalate obtained in the preceding step (i) were suspended in 150 ml of dichloroethane and 150 ml of water. To the suspension was added a saturated sodium hydrogen carbonate solution, so as to make the solution basic. The solution was stirred vigorously for 10 minutes. The layer of the organic solvent was then recovered by separation. The resulting layer was washed with water and dried over sodium sulphate. After the solvent is then distilled off under a reduced pressure, the resulting viscous oily material was purified by means of silica gel column chromatography (solvent for elution: the mixed solvent of n-hexane.ethyl acetate), thereby obtaining the object as the free base. This material was pale yellowish and transparent viscous liquid. (Yield: 25.2 g).

Refractive index: $n_D^{20}$ 1.5395.

Specific gravity: $d_{20}^{20}$ 1.1485.

Measurement value of infrared absorption spectrum: $v_{max}^{film}$ cm$^{-1}$ 1736 (Ester).

EXAMPLE 2

Production of
2-trifluoromethyl-10-[3-(3-enanthyloxypyrrolidino)-
propyl]-phenothiazine (i) According to the procedure of the preceding Example 1, (i), 8.6 g of 2-trifluoromethyl-10-[3-(3-hydroxypyrrolidino)-propyl]-phenothiazine.hydrochloride and 3.3 g of enanthylchloride were subjected to the reaction. The oxalate of the object was thus obtained.

Melting point: 116°–118° C.

Yield: 10.3 g.

Measurement value of infrared absorption spectrum: $\nu_{max}^{Nujol}$ cm$^{-1}$ 1728 (Ester).

(ii) The oxalate obtained according to the above step (i) was reacted and treated according to the procedure of the preceding Example 1, (ii) to obtain the free base of the object, which was pale yellowish viscous liquid.

Refractive index: $n_D^{20}$ 1.5507.

Specific gravity: $d_{20}^{20}$ 1.1849.

Measurement value of infrared absorption spectrum: $\nu_{max}^{film}$ cm$^{-1}$ 1738 (Ester).

EXAMPLE 3

Production of
2-trifluoromethyl-10-{3-[3-(10-undecenoyl)-oxypirrolidino]-propyl}-phenothiazine (i) According to the procedure of Example 1, (i), 8.6 g of 2-trifluoromethyl-10-[3-(3-hydroxypyrrolidino)-propyl]phenothiazine.hydrochloride and 3.9 g of 10-undecenoylchloride were reacted with each other. The oxalate of the object was thus obtained.

Melting point: 109°–111° C.

Yield: 10.8 g.

Value of infrared absorption spectrum: $\nu_{max}^{Nujol}$ cm$^{-1}$ 1730 (Ester), 1640 (Double bond).

(ii) The esters of the object obtained according to the above step (i) was reacted and treated according to the procedure of Example 1, (ii), to obtain the free base of the objects which was pale yellowish viscous liquid.

Refractive index: $n_D^{20}$ 1.5449.

Specific gravity: $d_{20}^{20}$ 1.1510.

Measurement value of infrared absorption spectrum: $\nu_{max}^{film}$ cm$^{-1}$ 1730 (Ester), 1640 (Double bond).

EXAMPLE 4

Production of
2-trifluoromethyl-10-[3-(3-palmitoyloxypyrrolidino)-
propyl]-phenothiazine (i) According to the procedure of Example 1, (i), 8.6 g of 2-trifluoromethyl-10-[3-(3-hydroxypyrrolidino)-propyl]-phenothiazine.hydrochloride and 6.0 g of palmitoyl chloride were reacted with each other. The esters of the object was thus obtained.

Melting point: 114°–116° C.

Yield: 11.8 g.

Measurement value of infrared absorption spectrum: $\nu_{max}^{Nujol}$ cm$^{-1}$ 1730 (Ester).

(ii) The esters of the object according to the above step (i) was reacted and treated according the procedure of Example 1, (ii), to obtain the free base of the object which was pale yellowish viscous liquid.

Refractive index: $n_D^{20}$ 1.5142.

Specific gravity: $d_{20}^{20}$ 1.0555.

Measurement value of infrared absorption spectrum: $\nu_{max}^{film}$ cm$^{-1}$ 1735 (Ester).

EXAMPLE 5

Production of
2-trifluoromethyl-10-[3-(3-caproyloxypyrrolidino)-
propyl]-phenothiazine 8.6 G. of 2-trifluoromethyl-10-[3-(3-hydroxypyrrolidino)-propyl]-phenothiazine.hydrochloride were dissolved in 100 ml of dichloroethane. To the solution were added drop by drop 3.0 g of caproylchloride at a room temperature with stirring. This mixture was heated under reflux for two hours. After cooling, 20 ml of methanol were added to said mixture, and the whole was stirred for about 1 hour. The resulting reaction mixture was washed, in turn, with water, aqueous potassium carbonate solution and water respectively, and dried over sodium sulphate. The solvent was distilled off under a reduced pressure. The resulting pale brown oily material was purified by means of silicagel column chromatography (solvent for elution: the mixed solvent of n-hexan.ethylacetate), thereby obtaining the object as the free base, which was pale yellowish viscous liquid.

Yield: 8.2 g.

Refractive index: $n_D^{20}$ 1.5543.

Specific gravity: $d_{20}^{20}$ 1.2035.

Measurement value of infrared absorption spectrum: $\nu_{max}^{film}$ cm$^{-1}$ 1735 (Ester).

EXAMPLE 6

Production of
2-trifluoromethyl-10-{3-[3-(2-ethylhexanoyl)-oxypyrrolidino]-propyl}-phenothiazine According to the procedure of the preceding Example 5, 8.6 g of 2-trifluoromethyl-10-[3-(3-hydroxypyrrolidino)-propyl]-phenothiazine.hydrochloride and 3.6 g of 2-ethylhexanoylchloride were subjected to the reaction, to obtain the object as the free base.

Yield: 8.1 g.

Refractive index: $n_D^{20}$ 1.5273.

Specific gravity: $d_{20}^{20}$ 1.1278.

Measurement value of infrared absorption spectrum: $\nu_{max}^{film}$ cm$^{-1}$ 1725 (Ester).

EXAMPLE 7

Production of
2-trifluoromethyl-10-[3-(3-undecanoyloxypyrrolidino)-
propyl]-phenothiazine According to the procedure of Example 5, 10.8 g of 2-trifluoromethyl-10-[3-(3-hydroxypyrrolidino)-propyl]-phenothiazine.hydrochloride and 6.2 g of undecanoylchloride were subjected to the reaction, to object the object as the free base. (Yield: 11.2 g)

EXAMPLE 8

Preparation for ampoules for injection (1)

| Formulation | |
|---|---|
| 2-Trifluoromethyl-10-[3-(3-enanthyloxypyrrolidino)-propyl]-phenothiazine | 50 mg |
| Benzyl alcohol | 15 mg |
| Sesame oil amounting to | 1 ml |

Using the above formulation, ampoules for injection were prepared by means of the conventional method for the production of the oily injection drugs. These ampouls for injection may be dosed in the ratio of 0.5–1 ml at intervals of 10–20 days by means of intramuscular or subcutaneous injection.

EXAMPLE 9

Preparation for ampoules for injection (2)

| Formulation | |
| --- | --- |
| 2-Trifluoromethyl-10-[3-(3-enanthyloxypyrrolidino)-propyl]-phenothiazine | 50 g |
| Lecithin | 10 g |
| Tween 80 | 0.1 g |
| Aluminium stearate | 1.0 g |
| Sesame oil amounting to | 1,000 ml |

Using the above formulation, ampoules for injection were prepared by means of the conventional method for the production of the oily injection drugs. These ampouls for injection may be dosed in the ratio of 0.5–1 ml at intervals of 10–20 days by means of intramuscular or subcutaneous injection.

What is claimed is:

1. Phenothiazine derivatives having the general formula:

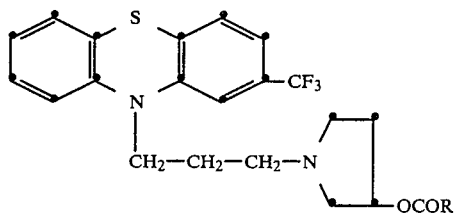

wherein R represents a straight or branched alkyl, alkenyl or aralkyl group having 5–15 carbon atoms and their pharmaceutically acceptable acid addition salts.

2. The phenothiazine derivative as claimed in claim 1, wherein said phenothiazine derivative is 2-trifluoromethyl-10-[3-(3-decanoyloxypyrrolidino)-propyl]-phenothiazine.

3. The phenothiazine derivative as claimed in claim 1, wherein said phenothiazine derivative is 2-trifluoromethyl-10-[3-(3-enanthyloxypyrrolidino)-propyl]-phenothiazine.

4. The phenothiazine derivative as claimed in claim 1, wherein said phenothiazine derivative is 2-trifluoromethyl-10-{3-[3-(10-undecenoyl)-oxypyrrolidino]-propyl}-phenothiazine.

5. The phenothiazine derivative as claimed in claim 1, wherein said phenothiazine derivative is 2-trifluoromethyl-10-[3-(3-palmitoyloxypyrrolidino)-propyl]-phenothiazine.

6. The phenothiazine derivative as claimed in claim 1, wherein said phenothiazine derivative is 2-trifluoromethyl-10-[3-(3-caproyloxypyrrolidino)-propyl]-phenothiazine.

7. The phenothiazine derivative as claimed in claim 1, wherein said phenothiazine derivative is 2-trifluoromethyl-10-{3-[3-(2-ethylhexanoyl)-oxypyrrolidino]-propyl}-phenothiazine.

8. The phenothiazine derivative as claimed in claim 1, wherein said phenothiazine derivative is 2-trifluoromethyl-10-[3-(3-undecanoyloxypyrrolidino)-propyl]-phenothiazine.

9. Anti-psychotic drugs which contains an anti-psychotically effective amount of a phenothiazine having the general formula:

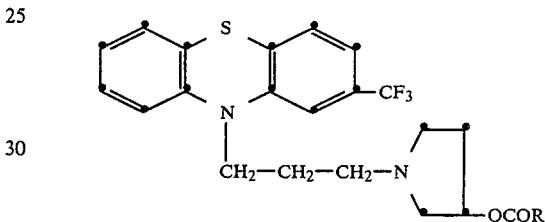

wherein R represents a straight or branched alkyl, alkenyl or aralkyl group having 5–15 carbon atoms or their pharmaceutically acceptable acid addition salts together with pharmaceutically acceptable excipients.

10. The anti-psychotic drug as claimed in claim 9, wherein the phenothiazine derivative is 2-trifluoromethyl-10-[3-(3-caproyloxypyrrolidino)-propyl]-phenothiazine.

11. The anti-psychotic drug as claimed in claim 9, wherein the phenothiazine derivative is 2-trifluoromethyl-10-[3-(3-enanthyloxypyrrolidino)-propyl]-phenothiazine.

* * * * *